United States Patent [19]

Blöst et al.

[11] Patent Number: 4,931,278
[45] Date of Patent: Jun. 5, 1990

[54] STORAGE-STABLE PREPARATIONS OF WHEAT VINASSE

[75] Inventors: Elly Blöst, Duesseldorf; Ute Welkert, Ratingen, both of Fed. Rep. of Germany

[73] Assignee: Allrutan Bio-Produkte GmbH, Duesseldorf, Fed. Rep. of Germany

[21] Appl. No.: 39,227

[22] Filed: Apr. 17, 1987

[30] Foreign Application Priority Data

Apr. 22, 1986 [DE] Fed. Rep. of Germany ....... 3613525

[51] Int. Cl.$^5$ .................. A61K 35/78; A61K 7/00; A61K 7/035; A61K 7/06
[52] U.S. Cl. .................... 424/195.1; 424/47; 424/69; 424/74; 424/466; 514/944; 514/960
[58] Field of Search ................. 424/47, 69, 466, 74, 424/195.1; 514/944, 960

[56] References Cited

U.S. PATENT DOCUMENTS 3,884,770  5/1975  Misselhorn .................... 203/82

FOREIGN PATENT DOCUMENTS 2050212  10/1970  Fed. Rep. of Germany ........ 203/82
1316896  5/1973  United Kingdom .

OTHER PUBLICATIONS

Härtel, "Weizentrockenschlempe als Komponente im Geflügelmastfutter?", Kraftfutter, Band 2, Feb. 1978.

*Primary Examiner*—John W. Rollins
*Attorney, Agent, or Firm*—Wegner & Bretschneider

[57] ABSTRACT

A storage-stable preparation, containing the ingredients of freshly recovered wheat vinasse, is prepared after optional removal of husks by grinding to colloidal size and drying under mild conditions, whereafter to the product thus obtained optionally are added fluxing agents, wetting agents, aroma ingredients and further powdery or oily vegetable extracts.

20 Claims, No Drawings

STORAGE-STABLE PREPARATIONS OF WHEAT VINASSE

The present invention relates to storage-stable preparations containing the ingredients of freshly recovered wheat vinasse and a process for preparing same.

In the spa of Rheindahlen (West-Germany), treatments with wheat mud baths have been carried out for years, which baths have proven to be useful in the treatment of rheumatic diseases and skin diseases. More particularly, surprising success was achieved with psoriasis patients and with patients suffering from joint troubles. These wheat mud baths have been prepared exclusively by using freshly recovered hot vinasse from the Rheindahlen Kornbrennerei (grain-alcohol plant), the Hans Rother Kornbrennerei and a liqueur factory in Werne. This is a vinasse obtained under mild distillation conditions, namely by stripping the alcohol with steam blown into the mixture. More specifically, the wheat vinasse is obtained by the so-called Bona Destillata distilling process according to the German Patent Specification No. 20 50 212.

A substantial disadvantage of these wheat mud baths is that always hot and relatively fresh wheat vinasse must be employed therefor, since upon cooling there arises the risk of bacterial infections and during storage at elevated temperatures over an extended period of time the valuable constituents are decomposed or destroyed so that the efficiency decreases.

It is the object of the present invention to develop storage-stable preparations which contain the ingredients of freshly recovered wheat vinasse so that they can be employed at any place and at any time desired. In developing such preparations it is also essential that the valuable ingredients are preserved and stabilized so that said preparations will remain at least comparable to wheat mud baths made from fresh hot wheat vinasse. Thorough and detailed investigations in the end resulted in the finding that said object can be attained by freeing, if necessary, the freshly recovered wheat vinasse of the husks and subsequently grinding it to colloidal size and drying the resulting material under mild conditions. The product as thus obtained is admixed, if desired, with fluxing agents, wetting agents, aroma ingredients and further powdery or oily vegetable extracts. In this state it may be packaged, stored, transported and used at any time for preparing a bath by mixing said preparation again with hot water. However, the product thus obtained may also be converted into the application forms of skin cream, gel, shampoo, face packs comprising collagen or effervescent tablets.

Thus, the present invention relates to storage-stable preparations containing the ingredients of freshly recovered wheat vinasse which are characterized in that they contain wheat vinasse which has been, if desired, freed of husks, has been ground to colloidal size and has, been dried under mild conditions, and optionally contain fluxing agents, wetting agents, aroma ingredients and further powdery or oily vegetable extracts.

The wheat vinasse employed in the present invention preferably is a wheat vinasse obtained from a distillation under mild conditions, namely by stripping the alcohol with steam blown into the fermentation mixture. Particularly preferred is a wheat vinasse obtained in the so-called Bona Destillata distilling process according to the German Patent Specification No. 20 50 212.

It is preferred that a fluxing agent is added to the dried preparation in order to ensure the flowability of the dried powder to be retained over an extended period of time. As the fluxing agents, mixtures of tricalcium phosphate and silica have proven to be particularly suitable. These fluxing agents are added to the powder in an amount of 1 to 5%, and preferably of about 2%. The powder may further be admixed, if desired, with powdery or oily vegetable extracts. For this purpose, camomile extract powder is particularly suitable. Further suitable additives are rosemary, balm-mint, citrus camphor, menthol, wheat germ oil, soybean oil and lecithin. The addition of solid surfactants such as sodium lauryl sulfate should be limited to relatively small amounts, since otherwise the activity of the ingredients of the wheat vinasse is reduced.

More particularly, in order to preserve the valuable ingredients of the wheat vinasse, not only is the distillation to be carried out under mild conditions, but also drying must be effected under mild conditions as well. Spray-drying has proven to be particularly suitable, in which a dry powder containing from 2 to 4% of residual moisture can be obtained from a 5% vinasse in one operational step and without long-lasting thermal stress. As the product thus obtained tends to agglomerate and lose its flowability after some time, it is preferred to add a fluxing agent to the preparation. It is possible to add still further powdery or oily vegetable extracts to the products in order to enhance the activity.

For preparing a bath with the powdery product prepared according to the invention it is sufficient, for example, to charge 75 g of said product into the bathtub and to allow water having a temperature of about 35° C. to 40° C. to run in. However, if it is desired to enhance the effect, then 2 or 3 packages of 75 g of the preparation may be used per bath. Then, the bath should be allowed to exert its action for about 20 to 25 minutes. The bath should be followed by a period of rest of about 1 hour in the same way as appropriate for baths made from freshly prepared wheat vinasse.

In comparative tests it has been found that in the dry storage stable preparation to be used for baths according to the invention the contents of vitamins, amino acids and trace elements are approximately the same as that of wheat mud baths using freshly obtained uncomminuted wheat vinasse. On the other hand, tests with uncomminuted vinasse and vinasse having been dried on drum driers have shown that baths prepared therefrom are substantially less active and contain substantially lesser amounts of valuable active substances.

For the preparation of skin cream, gel, shampoo, face packs comprising collagen or effervescent tablets it is particularly recommended to separate the husks prior to grinding to colloidal size. This is most simply accomplished by decantation. It has been found that the husks are substantially more difficult to grind to colloidal size, while, on the other hand, they do not contain the valuable ingredients of the freshly recovered wheat vinasse.

For the preparation of a skin cream, the dried product prepared according to the invention can be incorporated into a conventional base for skin creams. Oil-in-water and water-in-oil emulsions based on lanolin have proven to be particularly suitable. The amount of the storage-stable preparation made according to the invention is from 10 to 15% by weight, and preferably 10% by weight.

Skin-compatible sugar-surfactants have proven to be most suitable for stabilizing.

For the preparation of a gel, conventional pharmacologically compatible gel bases of hydrocolloids may be employed. Since these gels are mostly applied in the form of a pack, they may be prepared with a wheat vinasse which still contains the husks. Nevertheless, here also a material is preferred to be used which has previously been freed of the husks. The gel may contain between 5 and 25% by weight of the product of the invention, as finally the packs are removed by washing.

For the preparation of a hair shampoo, also up to 10% of wheat vinasse freed of husks, ground to colloidal size and dried under mild conditions according to the invention can be used. Here, sugar-surfactants and other skin-compatible detergents can also be employed as the wetting agents.

A further interesting form of application are face packs comprising collagen, in the course of the preparation of which the preparations according to the invention are already incorporated. Collagen-comprising face packs which may be employed according to the invention have so far been offered without such additives by the Dr. Suwelack GmbH in Billerbeck (West Germany). Suitable spongy collagen preparations, have been described, for example, in German Unexamined Patent Application DE-OS No. 32 03 957. In such face packs there may also be incorporated from 3 to 15% of the preparations of the invention. The collagen packs are moistened briefly prior to the application thereof and then placed on the skin of the face. They allow the active ingredients of the wheat vinasse uniformly to penetrate into the underlying skin.

It is also possible to use the storage-stable preparations of the invention in the form of effervescent tablets, so that it is possible to package and store the products of the invention compactly. Upon dissolution of the effervescent tablets, the active ingredients are released again and then can display their action in a bubbling and foaming bath. Such effervescent tablets are particularly suitable for infant baths and for export. The bubbling effect of the effervescent tablets is accomplished in the usual manner by a solid alkali hydrogencarbonate and a solid acid such as citric acid which, separated from each other in space, are compressed together into tablets.

Investigations with the preparations of the invention have shown that not only upon the application of baths, but also upon the applications of skin cream, gel, shampoo, face packs comprising collagen and effervescent tablets, successful healing and alleviation effects are achieved. Thus, the preparations according to the invention can be used not only for general care of the skin and for prophylaxis, but also in the cases of rheumatic diseases, psoriasis, arthrosis, acne, vein inflammation and varicose veins, effusions of blood and sprains.

For the preparations of skin cream and gel it has proven to be advantageous to add sorbic acid ozonide as a further component. Sorbic acid ozonide causes active oxygen to be released and is capable of enhancing the efficiency of the other components. A positive effect on storage-stability and long-term stability of creams and gels has further been observed.

The manufacture and composition of the preparations according to the invention are further illustrated by way of the following non-limiting examples.

EXAMPLE 1

A freshly recovered hot wheat vinasse, obtained from Rheindahlener Kornbrennerei in the so-called Bona-Destillata process according to German Patent No. DE-PS No. 20 50 212, having a solids content of from 4 to 5%, was ground to colloidal size and spray-dried. The residual moisture was 2–4%. After the drying procedure, 2% of a fluxing agent and 0.1% of camomile extract powder were admixed. The fluxing agent was a mixture of 50% of tricalcium phosphate and 50% silica. The preparation thus obtained was filled into plastic bags, each containing 75 g of the preparation, and the bags were sealed. The dry preparation was storage-stable without undergoing any change in quality for several months.

The contents of 1, 2 or 3 of said plastic bags were charged into a bath-tub for use, and the tub was filled with water of 35° C. to 40° C. The efficiency of such a bath was absolutely comparable to that of wheat mud baths using hot fresh wheat vinasse.

The analytical examination of the dry storage-stable preparation of the invention resulted in the following values: 100 g of the preparation contained 30 I.U. of vitamin A and 0.16 mg of vitamin E (total tocopherol). There were further found 11.5 mg of vitamin $B_1$, 44 mg of vitamin $B_2$, 28 mg of vitamin $B_6$, 0.84 mg of nicotinamide, 0.115 mg of pantothenic acid, 2.45 mg of biotin and 5.7 mg of folic acid.

Free amino acids were found in concentrations in micromoles/ml:

| | |
|---|---|
| Taurine | 0.537 |
| Aspartic acid | 0.397 |
| Threonine | 0.223 |
| Serine | 0.549 |
| Asparagine | 0.097 |
| Glutamic acid | 0.769 |
| Glutamine | 0.039 |
| Glycine | 0.337 |
| Alanine | 0.960 |
| Valine | 0.441 |
| Cystine | 0.116 |
| Methionine | <0.005 |
| Isoleucine | 0.283 |
| Leucine | 0.789 |
| Tyrosine | 0.069 |
| Phenylalanine | 0.272 |
| Ornithine | 0.469 |
| Lysine | 0.415 |
| Histidine | 0.165 |
| 3-Methylhistidine | ~0.07 |
| Tryptophane | ~0.07 |
| Arginine | <0.005 |
| Cysteic acid | ~1.000 |

The following trace elements and electrolytes have been determined:

Co $(1.50 \pm 0.25) \cdot 10^{-9}$ g per 1 g of sample
Se $(5.80 \pm 1.84) \cdot 10^{-9}$ g per 1 g of sample
Sb $(6.24 \pm 1.40) \cdot 10^{-9}$ g per 1 g of sample
Cd $(6.40 \pm 0.90) \cdot 10^{-9}$ g per 1 g of sample
As $(12.40 \pm 1.80) \cdot 10^{-9}$ g per 1 g of sample
Pb $(26.00 \pm 2.40) \cdot 10^{-9}$ g per 1 g of sample
Rb $(0.26 \pm 0.05) \cdot 10^{-6}$
Zn $(3.83 \pm 0.35) \cdot 10^{-6}$ g per 1 g of sample
Fe $(4.58 \pm 0.42) \cdot 10^{-6}$ g per 1 g of sample
Mn $(43.00 \pm 4.50) \cdot 10^{-6}$ g per 1 g of sample
Na $(52.00 \pm 14.80) \cdot 10^{-6}$ g per 1 g of sample
K $(933.00 \pm 185.00) \cdot 10^{-6}$ g per 1 g of sample The elements As, Pb and Cd were determined by means of atomic absorption spectrometry, and the other 9 elements were determined by neutron-activation analysis.

Patients suffering from rheumatism, from psoriasis and from both diseases were examined. 96% of the persons suffering from rheumatism were absolutely free of complaints, felt a distinct improvement or found a perceivable alleviation after 6 to 12 baths. Only 3.9% of the patients did not report any improvement. Among the psoriasis patients 6% were absolutely free of complaints after 10 baths, 37% felt a distinct improvement, and the remaining patients reported at least a perceivable improvement. Among the patients suffering from both rheumatism and psoriasis vulgaris, the treatment was effective in 89% of the cases.

EXAMPLE 2

A freshly recovered hot wheat vinasse from the Rheindahlener Kornbrennerei obtained from the so-called Bona-Destillata process according to German Patent No. DE-PS 20 50 212 and having a solids content of from 4 to 5% was decanted, whereby the husks were almost completely separated off. The remaining residue was ground to colloidal size and spray-dried. The residual moisture was 2-4%. The product thus obtained was further processed in the following manners:

Skin Cream: A conventional commercial skin cream based on an emulsion of lanolin in water was mixed by intense stirring with 10% by weight of the spray-dried product and 1% by weight of a sugar-surfactant. A well inunctable skin cream was obtained.

Hair Shampoo: A conventional commercial hair shampoo was triturated with 8% by weight of the spray-dried product and 1% by weight of a sugar-surfactant. A well foaming hair shampoo was obtained.

Gel: A conventional commercial gel base (hydrocolloid) was mixed with 15% by weight of the spray-dried product. A well applicable paste was obtained which could be administered as a pack on varicose veins and the like.

Collagen-Comprising Face Pack: The base formulation of the collagen face packs of the firm Dr. Suwelack GmbH in Billerbeck, West Germany, was admixed with 10% of the spray-dried product, and the mixture was further processed in the conventional manner to give face packs. The face packs had the same mechanical properties as the previously commercially available products, while, however, they contained the ingredients of fresh wheat vinasse. Such face packs caused a distinct stretching and regeneration of the skin.

Effervescent Tablets: A conventional commercial base composition for effervescent tablets containing sodium hydrogen-carbonate and citric acid was admixed with 10% by weight of the spray-dried product and 5% by weight of a sugar-surfactant. When the resulting tablet was thrown into warm water, a bubbling and foaming bath containing the ingredients of fresh wheat vinasse was formed.

What is claimed is:

1. Storage-stable preparation containing an ingredient of freshly recovered wheat vinasse. which has been ground to colloidal size and dried under mild conditions.

2. Preparation of calkaim 1, wherein the freshly recovered wheat vinasse has been freed from husks.

3. Preparation of claim 2, further containing one or more additional ingredients from the class consisting of fluxing agents, wetting agents, and aroma ingredients.

4. Preparation according to claim 2, in the form of a skin-cream, gel, shampoo, face pack comprising collagen or effervescent tablets.

5. Preparation of claim 1, wherein the freshly recovered wheat vinasse has been obtained from a distillation under mild conditions by stripping alcohol from a fermentation mixture with introduced steam.

6. Preparation of claim 1, wherein the drying under mild conditions has been effected by spray-drying.

7. Preparation of claim 1 wherein the drying under mild conditions has been effected by freeze-drying.

8. Preparation of claim 1, further containing one or more additional ingredients from the class consisting of fluxing agents, wetting agents, and aroma ingredients.

9. Preparation of claim 1, in the form of a skin cream, gel, shampoo, face pack comprising collagen, or effervescent tablets.

10. Preparation of claim 1, in the form of a dry bath preparation.

11. Preparation of claim 10, further containing a fluxing agent.

12. Preparation of claim 10, wherein the freshly recovered wheat vinasse has been obtained from a distillation under mild conditions by stripping alcohol from a fermentation mixture with introduced steam.

13. Process for manufacturing a storage-stable preparation containing an ingredient of freshly recovered wheat vinasse, comprising grinding the freshly recovered wheat vinasse to colloidal size and then drying the freshly recovered wheat vinasse under mild conditions.

14. Process according to claim 13, wherein the freshly recovered wheat vinasse has been obtained from a distillation under mild conditions by stripping alcohol from a fermentation mixture with introduced steam.

15. Process according to claim 13, wherein the drying under mild conditions is effected by spray-drying.

16. Process according to claim 13, wherein the drying under mild conditions is effected by freeze-drying.

17. Process according to claim 13, further comprising freeing the freshly recovered what vinasse from husks prior to the grinding.

18. Process according to claim 13, wherein the product thus obtained is further processed to give a skin-cream, gel, shampoo, face pack comprising collagen or effervescent tablets.

19. Process for preparing a dry storage-stable preparation for baths, comprising grinding a wheat vinasse to colloidal size and then drying the wheat vinasse under mild conditions.

20. Process according to claim 19, wherein the wheat vinasse has been obtained from a distillation under mild conditions by stripping alcohol from a fermentation mixture with introduced steam.

* * * * *